United States Patent
Kane et al.

(10) Patent No.: US 9,994,714 B2
(45) Date of Patent: Jun. 12, 2018

(54) SILICA PROTECTED PIGMENTS FOR USE IN ARTIST MEDIA

(71) Applicant: Thomas E. Kane, Tyrone, PA (US)

(72) Inventors: Thomas E. Kane, Tyrone, PA (US); Brian A. Jones, Bellefonte, PA (US)

(73) Assignee: Thomas E. Kane, Bellefonte, PA (US)

( * ) Notice: Subject to any disclaimer, the term of this patent is extended or adjusted under 35 U.S.C. 154(b) by 14 days.

(21) Appl. No.: 14/891,278

(22) PCT Filed: May 16, 2014

(86) PCT No.: PCT/US2014/038449
§ 371 (c)(1),
(2) Date: Nov. 13, 2015

(87) PCT Pub. No.: WO2014/186740
PCT Pub. Date: Nov. 20, 2014

(65) Prior Publication Data
US 2016/0108244 A1    Apr. 21, 2016

Related U.S. Application Data

(60) Provisional application No. 61/824,177, filed on May 16, 2013.

(51) Int. Cl.
| | |
|---|---|
| *C09B 67/08* | (2006.01) |
| *C09B 65/00* | (2006.01) |
| *C09B 67/02* | (2006.01) |
| *A61K 8/25* | (2006.01) |
| *A61Q 1/02* | (2006.01) |
| *A61K 8/02* | (2006.01) |
| *B05D 1/18* | (2006.01) |
| *B05D 7/00* | (2006.01) |
| *C09D 7/12* | (2006.01) |

(52) U.S. Cl.
CPC ........ *C09B 67/0007* (2013.01); *A61K 8/0241* (2013.01); *A61K 8/25* (2013.01); *A61Q 1/02* (2013.01); *B05D 1/18* (2013.01); *B05D 7/57* (2013.01); *B05D 7/58* (2013.01); *C09B 65/00* (2013.01); *C09B 67/0013* (2013.01); *C09B 67/0097* (2013.01); *C09D 7/1225* (2013.01); *A61K 2800/412* (2013.01); *A61K 2800/61* (2013.01); *A61K 2800/651* (2013.01)

(58) Field of Classification Search
None
See application file for complete search history.

(56) References Cited

U.S. PATENT DOCUMENTS

| | | | |
|---|---|---|---|
| 2,490,662 A | 12/1949 | Thomsen | |
| 3,549,317 A * | 12/1970 | Dorn | .............. B01J 20/103 423/339 |
| 4,199,370 A | 4/1980 | Brand | |
| 4,468,420 A * | 8/1984 | Kawahara | ............... C03C 17/25 106/287.34 |
| 4,530,725 A | 7/1985 | Ostertag et al. | |
| 4,851,049 A | 7/1989 | Wienand et al. | |
| 5,073,408 A | 12/1991 | Goda et al. | |
| 5,114,760 A | 5/1992 | Takemura et al. | |
| 5,232,781 A | 8/1993 | Takemura et al. | |
| 6,113,682 A | 9/2000 | Shin et al. | |
| 6,117,435 A | 9/2000 | Painter et al. | |
| 6,355,260 B1 | 3/2002 | Tanaka et al. | |
| 6,511,672 B2 | 1/2003 | Tan et al. | |
| 6,648,958 B2 | 11/2003 | Anselmann et al. | |
| 8,277,785 B2 | 10/2012 | Simard et al. | |
| 8,366,814 B2 | 2/2013 | Jones et al. | |
| 8,658,184 B2 | 2/2014 | Schulz et al. | |
| 2004/0137246 A1 | 7/2004 | Fristad et al. | |
| 2004/0177789 A1* | 9/2004 | Heider | .................. C09C 1/0009 106/499 |
| 2005/0069704 A1 | 3/2005 | Rathschlag et al. | |
| 2008/0044366 A1 | 2/2008 | Dumousseaux | |
| 2009/0053524 A1 | 2/2009 | Yamada et al. | |
| 2009/0227711 A1* | 9/2009 | Carlini | ................ C09B 67/0013 524/90 |
| 2009/0246674 A1* | 10/2009 | Carlini | .................. B82Y 30/00 430/110.2 |
| 2013/0081484 A1 | 4/2013 | Jones et al. | |

OTHER PUBLICATIONS

Taylor, et al.; painting by numbers; Adv. Mater. 2011, vol. 23 pages. 2554-2570.
Wang, et al.; Synthesis of silica encapsulated PTCD core shell nanoellipsoids; Chem. Mater. vol. 23 pages. 4748-4755 (2011).
International Search Report from counterpart PCT International Application No. PCT/US2014/038449.
Search History from counterpart PCT International Application No. PCT/US2014/038449.
Written Opinion of the International Searching Authority from counterpart PCT International Application No. PCT/US2014/038449.

* cited by examiner

*Primary Examiner* — Melvin C Mayes
*Assistant Examiner* — Colette Nguyen
(74) *Attorney, Agent, or Firm* — John F. A. Earley, III; Frank J. Bonini, Jr.; Harding, Earley, Follmer and Frailey, P.C.

(57) ABSTRACT

A pigment particle for use in artist color media comprises a silica containing core particle having pore channels formed therein, at least one colorant present in the pore channels in at least part of the silica particle, and a nonporous silica layer coated over the pore channels. A method of manufacturing colored particles for use in artist color media comprises providing a core silica particle having pore channels formed therein, loading at least one colorant into the pore channels of the particle, and depositing a silica layer over the pore channels using fluorosilicic acid. Another method of manufacturing colored particles for use in artist color media comprises providing a porous silica particle having pore channels formed therein, and depositing a silica layer over the pore channels using a fluorosilicic acid where a colorant is present in the fluorosilicic acid.

9 Claims, No Drawings

SILICA PROTECTED PIGMENTS FOR USE IN ARTIST MEDIA

CROSS-REFERENCE TO RELATED APPLICATION

This application claims priority to and the benefit of U.S. provisional Patent Application Ser. No. 61/824,177 filed on May 16, 2013. Said U.S. Provisional Patent Application Ser. No. 61/824,177 is hereby incorporated herein by reference in its entirety.

BACKGROUND

Novel synthetic chemistry and formulations are continuously being developed to improve the optical performance and longevity of commercial and consumer-grade paints and coverings. Formulations are tailored to accommodate a variety of environmental factors and the substrates onto which the paints are being applied.

The paints employed by fine artists are generally made using traditional formulations employing historical manufacturing practices. Today there is a strong interest amongst artists for paints that are compositionally similar to the paints employed by the historical art masters, but where they also exhibit improved long term color stability.

In many cases the pigments or dyes employed in fine arts paints and pastels are highly susceptible to color degradation over time. Environmental exposure, UV light degradation originating from sunlight and room light, atmospheric oxidation, and reaction with other compounds present in the painted substrate are all common drivers that result in color fading. In the interest of artwork longevity, modern artists are forced to avoid traditional paints or pastels that are known to fade or degrade over time. Manufacturers of art supplies have also avoided pigments or dyes that, while desirable for their color brilliance or other optical properties, are known to be difficult to work into paints through chemical reactivity, resistance to uniform dispersion, toxicity, or undesirable changes in color hue or tone after the paint has dried or cured.

Classical paints also commonly employ silica particles as bulk filler or in some cases as a means to enhance the paint luster or transparency. We present an improved method for protecting pigments or dyes where the protecting layer is silica, and where the pigment or dye provides all of the desirable color and other optical properties the fine art painter desires.

For the purpose of this disclosure the terms 'artist color media' relates to colored materials applied to a solid surface by artists in the production of artwork. Artist color media may include paints, pastels, colored pencils, chalks, stains, glazes, and clays. Example solid surfaces may be essentially flat or contoured and may include canvas, paper, wood, glass and stone. The term 'traditional artist color media' relates to color media with compositions used for more than about 100 years.

Color and Colorants

'Color' is the general term which applies to the entire subject of visible light. Any given color can be described in terms of its value and hue. 'Hue' is the term for the pure spectrum colors commonly referred to by the 'color names'—red, orange, yellow, blue, green violet—which appear in the rainbow. 'Value' is defined as the relative lightness or darkness of a color.

'Pigments' are inorganic or organic, colored, white or black materials which are essentially insoluble in the medium in which they are incorporated. 'Dyes', unlike pigments, do dissolve during their application and in the process lose their particulate structure. It is thus by physical characteristics rather than by chemical composition that pigments are most often differentiated from dyes.

For the purpose of this disclosure the term 'colorant' relates to any free pigments or dyes, regardless of their solubility, which are used to create a color in the silica particle. 'Pigment' relates to colorants that are insoluble, and 'dyes' relate to colorants that are soluble in the desired solvent.

The term 'colored particle' refers to the silica particle substrate which contains at least one colorant, without any silica encapsulation layer. The term 'pigment particle' refers to the final silica encapsulated colored particle.

Encapsulation of Pigments

The presence of the encapsulating silica in accordance with the invention helps to passivate the surface properties and functionality of the core colored particle, thereby enabling good pigment particle dispersability in a variety of paint and pastel compositions. Pure silica surfaces are preferable to surfaces containing other metal species due to the increased reactive nature of metal species. Encapsulating silica layers are therefore preferably greater than 90% wt/wt silica, and less than 0.1% wt/wt with respect to metal species. Additionally, the surface deposited silica layer is preferably of nanoscale thickness, and optically transparent.

The core-shell type silica-encapsulated colorants in accordance with the invention provide a benefit that the composition of classic paint or pastel compositions can be standardized for such encapsulated pigments without requiring a customized reformulation for a particular pigment type, which is most often required. The silica encapsulation of colorants can therefore enable one to have a different artist color media by merely changing the core colorant composition (pigment) but not the surface shell composition.

Silica Layer Formation Processes

There exist various processes by which the silica shell can be provided on pigment particles. Most of these methods involve a sol-gel reaction. In this process the silica precursor is reacted in a series of hydrolysis and polymerization reactions to form a colloidal suspension, or sol, which is then precipitated onto the pigment core to provide a thin film coating of silica on the core pigment particle. See U.S. Pat. No. 6,113,682 which discloses methods for preparing bulk silica via use of aqueous sodium silicate and pH adjustment, known generally in the art as the sol-gel process.

Another sol-gel system commonly employed to produce silica coatings is based on the hydrolysis of an organosilane precursor reagent such as tetraethoxysilane (TEOS) or tetramethoxysilane (TMOS) in the presence of either water or an alcohol solvent, followed by condensation polymerization of the silicic acid intermediate under basic or acidic conditions (often referred to as a Stober-type method, first published by Stober, Fink and Bohn in *J. Colloid Interface Sci.* 1968, v. 26, p. 62 the text of which is incorporated herein by reference).

Sol-gel processes are difficult to control and are unable to yield silica particles with narrow distributions of particle sizes or film thicknesses. As a process for creating uniform nanoscale layers of silica on pigment particles, sol-gel processes require tight control of all chemical precursors and careful metering means of acid/base reagents, which in turn results in complex processes which are vulnerable to small variability. As compared to bulk quartz for example, silica coatings created from organosilane precursors such as TEOS and TMOS yields lower density silica matrices as a result of liberation of ethanol or methanol, respectively, when the silica layer is formed. Drying the silica layer serves to remove the liquid phase from the condensed gel, yielding an amorphous, nano-porous glass or micro-crystalline ceramic. Subsequent thermal treatment (firing or sintering) must be performed in order to favor further polycondensation, reduce porosity in the layer, and enhance mechanical properties. In the absence of thermal post-processing, TEOS and TMOS-based silica layers have comparatively poor mechanical strength and can crush or delaminate when subsequent pressure or abrasion is applied to the pigment particles.

Core Silica-Containing Particles

It well known to those skilled in the art that particle size (diameter) can contribute to the degree of optical transparency of the bulk media containing the particles. This behavior relates to the size of the particle relative to the wavelength of the illuminating light. As the particle size approaches the wavelength of the illuminating light the transparency of the bulk media increases. In some applications (for example, cosmetics), transparency is an optical property to be controlled. This control is in part possible by controlling the particle size. Pigment particle sizes suitable for artist color media preferably ranges from 1 to 100 µm, in diameter, and more preferably 5 to 50 µm in diameter. The shape of the particle has also been demonstrated to contribute to the optical properties of the pigment.

With respect to manufacturability of paints and pastels, uniformity and standardization of the pigment particles is desirable. Employing silica particles as substrates that standardize the shape and size of the pigment particles allows for simplification of paint and pastel formulations. Employing silica particles with a specific size and porosity provides a simple means to control the colorant load, and therefore the color intensity and hue formulations may also be standardized.

Core silica containing particles provide a substrate with which to apply colorants, where the result is a colored particle having uniform or well controlled size and shape, as well as colorant load. For the purpose of this disclosure the terms 'core particles' and 'core silica-containing particles' represent colored pigment particles where the center substrate is composed of silica or silica containing compositions.

For the purpose of this disclosure core silica-containing particles may be spherical or irregularly shaped. Core particles may include other elements beyond silicon, oxygen, and hydrogen; however core particles having a high ($SiO_2$) composition ensure effective bonding to the deposited silica encapsulating layer of the invention. Preferably, in accordance with the invention, the $SiO_2$ composition of the core particle is at least 50% by weight. More preferably, the ($SiO_2$) groups in the core particles preferentially reside on the outer surface of the particle where they are available for additional silica deposition. Core particles may be essentially nonporous or porous. The amount of colorant loading is dependent on the available surface area, and pore volumes (if any) of the core particle, where bulk colorant may accumulate.

Porous Silica Containing Particles: Spherical Porous 'HPLC' Silica

Examples of porous silica particles in this disclosure are predominantly spherical, amorphous, and appear white in color in the absence of any chemical treatment. Such particles are commercially available from a variety of suppliers and are commonly used as stationary phase substrates in high pressure liquid chromatography (HPLC) applications. HPLC particles are manufactured with tightly controlled silica purity, particle size, porosity, and surface area. For this application it is recognized that equally suitable porous silica particles may have relaxed tolerances with respect to HPLC-grade silica particles, however control of these physical properties in general can result in greater consistency with respect to the optical and color properties of the finished pigment particle.

In the case of porous silica particles, the pores are filled with colorant materials and the particles assume the color of the colorant. The degree to which the silica particle can assume the color (described here as the hue or value) is largely based on (1) the concentration of the colorant in or on the particle, (2) the surface area of the particle, and (3) the pore volume of the particle.

Nonporous Silica Containing Particles: Talc

Talc is a layered hydrous magnesium silicate of general empirical formula $Mg_3Si_4O_{10}(OH)_2$, that is a naturally occurring mineral and usually ground to a fine powder. The talc employed in this disclosure is bright white, although naturally occurring colored examples are commercially available. Talc has a high resistance to acids, alkalies and heat. The hydroxy groups normally are internal to the magnesium layer and are not accessible to water except at the edges of the silicate sheet. Thus, conventional talc powder is a hydrophobic material that easily blends and disperses with organic media including polymers but is not easily dispersed in aqueous solvents.

The composition of talc is approximately 64% $SiO_2$. The crystalline structure of talc consists of magnesium sandwiched between silica sheets, rendering the outermost surface predominantly Si—O units which are readily available for additional silica deposition. Talc is essentially nonporous and the surface area of talc increases with decreasing particle size in general agreement with the surface area vs. particle diameter. (see Foster, J; Doll, J. "Particle Size Effect on Talc Lubricant Activity". American Association of Pharmaceutical Scientists 2004 Annual Meeting Poster Session, the text of which is incorporated herein by reference). In cases where the colorant is loaded onto the outer surface of the talc particles, the amount of colorant load predominantly relates to the surface area and particle size.

DESCRIPTION OF RELATED ART

Colored Particles Derived from Bulk Glass Melt

Silica encapsulated pigments have been used in artist color media for centuries. A common example from history is smalt, a finely ground cobalt-containing glass used in 16th-century Renaissance paintings as a blue pigment.

Smalt is prepared by first melting together cobalt oxide to molten glass. When poured into cold water, the blue melt disintegrates into particles which are then ground. Several grades of smalt were made according to cobalt content and grain size Smalt has been historically important as a pigment in painting and for surface decoration of other types of glass, ceramics, and other media.

A more recent reference includes U.S. Pat. No. 8,658,184 where colored glass flakes suitable for cosmetics applications are manufactured from inorganic colorants added directly to the liquid glass melt and subsequently cooled and ground into particle flakes.

Because the colorants must be thermally stable at temperatures employed in melting glass (e.g., greater than 700° C.), only inorganic species are usually suitable to the process. Limited colorants are available that can withstand the temperatures required to melt glass. The process also results in regions on the surface where the colorant is exposed. Leaching of the colorant over time is therefore possible. In cases where the colorant is toxic this is especially undesirable. Mechanical grinding bulk colored glass into particles also limits the control on particle size distribution, requiring follow on size classification processes.

Sol-Gel Particle Formation with In-Situ Colorant Homogenously Distributed.

U.S. Pat. No. 6,303,149 discloses a process for preparing sol-gel microcapsules for cosmetic applications. The microcapsules contain colorant which was loaded in-situ to the sol-gel process and are present throughout the resulting silica particle. The process is conducted in two steps: (a) creating an oil-in-water emulsion by emulsification of a water insoluble solution comprising the sol-gel precursors and the molecules to be loaded, in an aqueous solution under appropriate shear forces; (b) mixing and stirring said emulsion with an aqueous solution at a suitably selected pH to obtain loaded sol-gel microcapsules in suspension. The emulsion-based process is limited to polar colorants which are soluble in the aqueous silicate solution and yields wide particle distributions. In cases where the colorant is nonpolar or otherwise insoluble in the aqueous phase, chemical modification and preprocessing of the colorant is necessary. The process employed requires metering of the acid or base in order to carefully control the pH of the aqueous solution. Emulsion-based particle processes yield wide distributions of particle sizes and require classification, which can be wasteful for the colorant raw material.

Unencapsulated Colored-Coated Particles.

In Appl. No. 20080044366 the disclosure relates to compositions for cosmetic applications comprising particles having an inorganic core which is coated with an organic coloring substance. In this case the coloring substance is immobilized on the inorganic core via an intermediary organic anchoring layer (a 'binder') which has been chemically bonded to the core. In this example the bulk colorant remains completely exposed to the surrounding environment.

In U.S. Pat. No. 6,511,672 irregularly-shaped platelet pigment particles are surrounded with silica beads in an effort to diffuse and blur the pigment for cosmetic applications. Here the silica beads are separate components from the pigment and provide little or no enhancement of thermal or chemical resistance of the pigment particle.

Colored Particles Encapsulated by Synthetic Organic Polymers.

Cosmetic applications employ colored particles for comparatively short durations, e.g., presumably for less than 48 hours after application on the skin Prior to application unused cosmetics are often stored in enclosures capable of shielding light and environmental moisture. As such, long term stability (e.g., greater than 10 years) of the colored particle is not especially required. Indeed, rapid breakdown of the particles may be preferred when the cosmetic application is removed and disposed of. U.S. Pat. No. 6,117,435 discloses a colored particle for cosmetics applications where the silica bead core is coated with at least one pigment layer, and optionally encapsulated with a synthetic organic polymer outer layer. The colored particle may not exhibit appreciably greater heat stability or lightfast properties as compared to the raw pigment due to the poor performance of the polymer layer. In examples where a synthetic organic polymer outer layer is employed the outer coating is also composed of materials that are preferably not present in traditional artist color media.

In application Ser. No. 10/949,718 pigment granules are encapsulated in a water soluble coating which dissolves away after the encapsulated pigment granule is introduced into an aqueous medium. These encapsulation coatings are temporary and are used as a means to facilitate dissolution of the nude pigment.

In U.S. Pat. No. 6,113,682 irregularly shaped silica particles are first coated with titanium dioxide followed by encapsulation using an organosilane or silicone polymer. In this case the outer coating is tailored for improved skin-adhesion and spreadability, and skin color-expression in cosmetics, and employs silicone materials that are not found in traditional artist color media.

Bulk Pigment Particles Encapsulated by Silica Using Sol-Gel Techniques.

U.S. Pat. No. 6,355,260 discloses a silica coated inorganic pigment, where the silica layer is applied using the TEOS condensation method. Here again bulk pigments as core particles must be insoluble with respect to the aqueous TEOS solution. In order to complete the silica encapsulation the coated particles were subjected to sintering at 600° C. following the condensation reaction.

U.S. Pat. No. 8,277,785 discloses encapsulation of insoluble bulk pigment particles where the encapsulant layer ranges from 1 to 25% wt of the final particle. A desired effect from the silica layer is to increase pigment translucence for greater compatibility in cosmetics in contact with skin oil and moisture, indicating thicker layers. The method of silica deposition is not disclosed.

U.S. Pat. No. 8,287,637 B2 discloses nanoparticle pigment particles having a surface-associated sterically bulky stabilizer that are encapsulated in silica using the standard sol-gel type polymerization of TEOS. Both the core particle and encapsulated particle are nanoscale in size. Nanoscale products have a high mobility and generally unknown human toxicological effects. In some countries, particularly in Europe, nanoscale products associated with human exposure have been regulated or banned.

Uncolored Particles with Colorant Coating Encapsulated by Silica Using Sol-Gel Techniques.

In the case of U.S. Pat. No. 6,648,958 spherical silica particles are coated with titanium dioxide and iron(III) oxide followed by a sol-gel processes, where the sodium silicate slowly coats the particle with a shift in pH of the solution. The particles then undergo calcination at temperatures from 500° C. to 900° C. In this fashion the process is limited to pigments that are color stable to temperatures greater than 500° C. The encapsulating silica layer also contains sodium, which increases the reactivity of the particle with surrounding media.

Pigment Particles with Magnesium-Silica-Fluorine Encapsulation

U.S. Pat. No. 4,530,725 discloses lead chromate pigments with a precipitated coating containing silicon dioxide, wherein an aqueous pigment suspension is mixed with an aqueous $MgSiF_6$ solution. U.S. Pat. No. 4,851,049 discloses bismuth vanadate/molybdate pigments encapsulated employing the same process described in U.S. Pat. No. 4,530,725. In both cases the encapsulation procedure is very complicated, requiring the timed metering of the silica containing reagent and continuous measurement and adjustment of the solution pH. Further, the process does not produce a pure silica layer; the composition of the resulting layer contains roughly equal molar concentrations of silicon and magnesium.

SUMMARY OF THE INVENTION

It is commercially desirable to produce paints, pastels, and other artist color media using materials employed by the historical paint manufacturers, but with improved optical performance and chemical inertness. With respect to manufacturability of paints and pastels, uniformity and standardization of the pigment particles is also desirable. Employing silica particles as substrates that standardize the shape and size of the pigment particles allows for simplification of paint and pastel formulations. Employing silica particles with controlled size and porosity provide a simple means to control the colorant load and therefore color intensity and hue formulations may also be standardized.

According to the present invention we demonstrate colored pigment particles which are composed of colorants, silica or silica-containing species and silica coatings which are chemically compatible with traditional formulations employed in artistic color media. We also demonstrate where the particles exhibit superior resistance to chemical bleaching and thermal degradation as compared to raw pigments and dyes.

We also demonstrate simple and rugged methods to product colored pigment particles, where the encapsulation processes employs saturated silica fluorosilicic acid, where the methods do not require metering of reagents, continuous monitoring and tight control of the reaction, or other labor intensive processes. We also demonstrate the production of a silica layer that does not require sintering or other high temperature post processing.

DETAILED DESCRIPTION OF THE INVENTION

Silica Containing Particles

Particles employed in this invention fall within the range of 3-12 µm, which are suitable for maximizing desired optical properties. Another physical feature that is possible in silica containing particles is secondary structure, most notably porosity. Silica containing particles may be produced with pores that are localized on the surface of the particle (superficially porous particles) or where pores exist throughout the particle structure (fully porous particles). The presence of pores in the silica containing particle increase the surface area of the particle as well as providing nanoscale vessels for colorant to deposit.

For the purpose of this disclosure, the terms 'silica particle' and 'silica-containing particle' are both used to describe the core particle where the Si—O composition is at least 50% by weight, and is suitable for applying a silica encapsulating layer by means of the Liquid Phase Deposition (LPD) process as described.

Colorant Loading onto Particles

Colorant may be loaded onto the particles using several methods. In one preferred embodiment the particles are introduced to bulk colorant solution in a beaker and allowed to accumulate the colorant through direct exposure. In this case the loading rate may be increased through stirring or other means of agitation.

Another preferred method to load color onto the particles is to first prepare the silica in a 1" diameter×10" long glass column, similar to configurations commonly employed in liquid 'flash' chromatography. Here the column is arranged vertically with the bottom of the column partially occluded to prevent the particles from exiting while allowing the solution to readily pass. The colorant is loaded in the top of the column and percolates through the column. As the colorant solution traverses down the column path the colorant loads onto and onto the particles. Following loading the wet particles are removed and collected from the column.

In both of these methods the particle may be subsequently dried prior to the LPD process. In other examples the particles may simply be filtered and introduced to the LPD process while still wet. In still another example the LPD solution may also contain additional colorant following the initial loading process. In still another example, the colorant load process is applied concurrently with the LPD process, whereby uncolored silica particles are introduced into the supersaturated fluorosilicic acid LPD solution which also contains colorant.

In another preferred method to load colorant onto a silica containing particle, fine dry powdered colorant is applied directly to the particle. Coating silica particles with smaller colorant particles is a well-known dry coating means to those skilled in the art. This method of colorant loading may also be accelerated through agitation of the dry particle/colorant mixture or application of static electric fields to the dry mixture. Dry loading methods are preferred in cases where the colorants are highly insoluble. Two notable examples of colorants suitable for dry loading include carbon black and porphyrin-containing compounds such as the phalo family of organic colorants. In addition to the physical properties of the silica particle, the amount of dry colorant loading is also dependent on the general mesh size of the powdered colorant.

Selection of which colorant loading method is in part dependent on:
1. the polarity of the colorant molecules
2. the polarity of the solvent (if used)
3. the solubility of the colorant in the solvent
4. the solubility of the colorant in fluorosilicic acid solutions
5. the loading affinity of the colorant to the silica containing particle Two Mechanisms Related to Colorant Loading of Silica Particles Two general mechanisms are proposed to describe the color loading process:

Mechanism 1. physisorption or otherwise mechanical filling of the pores in the silica particle with the colorant, followed by the closing off of the pore with deposited silica, and Mechanism 2. physisorption or chemisorption of the entire silica surface with the colorant, followed by coverage of the silica surface with deposited silica.

For mechanism 1 the colorant is trapped within the pores. In this case the hue and/or value of the resulting color is dependent on the concentration and volume of colorant solution loaded, which is in turn dependent on pore size and pore volume, as well as the particle diameter.

For the colorant load process mechanism 1 where the colorant solution is viscous or exhibits poor wettability with the core silica surface, the loading process may be mechanically forced into the particle pores by means of a pumping or vacuum filtration process.

For mechanism 2 the color is dependent on the overall surface area of the particle (which is also related to the particle pore size and volume), as well as the chemical compatibility of the silica particle surface (e.g., polarity, surface charge, etc.) with respect to the chemical properties of the colorant. In the case where the colorant is highly soluble in the LPD solution it is anticipated that the loading mechanism is more related to mechanism 2.

Mechanism 2 also enables the use of substantially non-porous silica particles, with the amount of colorant loading being largely dependent on the diameter of the particle and the degree of loading (i.e., layer thickness) of the colorant. The LPD process may be subsequently used to encapsulate the colorant loaded nonporous particle in the same way as described in the experimental sections.

In cases where the core silica particle is porous, colorants are likely loaded into porous particles as a result of contributions from both mechanisms.

Encapsulation of Colorant Loaded Silica Particles Using the LPD Method.

Liquid phase deposition of a silica film on glass substrates from fluorosilicic acid solutions under mild conditions was first described in U.S. Pat. No. 4,468,420, which is incorporated herein by reference. In this process, a silica-saturated fluorosilicic acid solution was employed to deposit a layer of silica on a glass substrate.

The reversible reactions can be exploited to deposit, precipitate, and/or change composition through evaporative or distillative processes depending on choice of conditions. The equilibria of mixtures of fluorosilicic acid and silica have been explored in detail.

$$H_2SiF_6 + 2H_2O \rightleftharpoons SiO_2\downarrow + 6HF$$

$$5H_2SiF_6 + SiO_2\downarrow \rightleftharpoons 3[H_2Si_6 \cdot SiF_4] + 2H_2O \rightleftharpoons 3H_2SiF_6\ SiF_4\uparrow + 2H_2O$$

It is clear that several components are present in equilibrium in an aqueous solution of fluorosilicic acid. As these can vary in relative concentration, we refer to any stable, homogeneous liquid reaction product of silica, hydrogen fluoride and water in this invention as fluorosilicic acid. In the event that a change occurs which renders the homogeneous solution unstable with regard towards precipitation of solid silica in any form, the solution shall be referred to as being supersaturated with silica.

It is apparent from the equilibria described above that through increasing the relative concentration of a component through addition, or by reducing one by depletion, the balance can shift to either precipitate or dissolve silica. For example, addition of water to a silica saturated fluorosilicic acid solution renders it supersaturated, leading to solid silica precipitation or its deposition as a film.

Much of the development done on silica based LPD has dealt with deposition on silicon and glass. Silicon substrates have been extensively used with LPD in semiconductor manufacturing as a means of producing conformal insulating films with low dielectric constants. Film densities, impurity incorporation, the effect of annealing conditions and their associated influence on electrical behavior have been extensively studied. Studies involving deposition on glass have generally centered on altering visual properties, such as reflectivity or color.

U.S. Pat. No. 2,490,662 discloses the amount of silica needed to saturate a fluorosilicic acid solution increases with the molar concentration, and tabular data of moles silica dissolved versus fluorosilicic acid molar concentrations provided. It is therefore possible to controllably deposit a silica layer employing a dilution-driven LPD process employing a saturated silica fluorosilicic acid solution.

U.S. Pat. No. 5,073,408 discloses the deposition of a silica layer employing a dilution-driven LPD process where the shift in silica solubility in a saturated fluorosilicic acid solution is controlled by increasing the temperature.

In both dilution-driven and temperature-driven LPD methods a dense, smooth silica surface with a controlled thickness is achieved. Silica layers are also possible employing a combination of both methods. In each case the procedures are quite simple and require minimal or no attendance during the deposition process.

In U.S. Pat. Nos. 5,114,760 and 5,232,781 the LPD process yielded a colored silica layer, where the fluorosilicic acid solution included a soluble, acid-stable colorant.

In all of the above disclosures the LPD process is applied to large glass surfaces, such as optical lenses and plate glass windows. Application of the LPD process on microscale particles has not previously been disclosed.

LPD based silica films from a saturated fluorosilicic acid solution have been demonstrated to yield smoother surfaces having a lower surface area per square unit of space as compared to untreated glass substrates. The technology is employed in the solid state electronics industry to planarize and smooth silicon-based substrates. Application of this LPD technology to liners and containers is therefore an alternative method with which to achieve a smoother, essentially pure silica surface on the uppermost surface of a borosilicate liner or container. It is a superior process to standard leaching technologies as the leaching process leaves behind a comparatively high surface area, high surface energy substrate, which can compromise the completeness and uniformity of the final liner or container's deactivation coating.

EXAMPLES

Example 1: Cleaning Preparation of Silica Particles

For fully porous silica particles, HPLC 'Ultra II' silica particles (Restek Corporation, Bellefonte, Pa.) were first heated from room temperature to 400° C. at 5° C./min, and then held for 48 hours under a low flow of carrier air. The oven temperature was then reduced to approximately 100° C. and the silica particles were transferred while still hot into an airtight glass container and stored until ready for use.

For essentially nonporous silica containing particles, pharmaceutical grade 'Ultra Talc 3000 USP' talc powder was obtained from Ultra Chemical, Inc. (Red Bank, N.J.). The talc was treated to the same 400° C. heat cleaning process described above and then transferred while still hot into an airtight glass container and stored until ready for use.

Example 2: Preparation of Silica Saturated Fluorosilicic Acid (SSFA) Solution

Quartz wool (fiber diameter: 9 um) was first heat treated at 400° C. for 48 hours and then cooled and added to a 3.2M stock solution of fluorosilicic acid. At 1 hour intervals the suspension was vigorously shaken for 2 minutes over a period of 8 hours. The suspension was then stored in a freezer at ca. 3° C. Immediately prior to use, the SSFA suspension was filtered through a 0.45 μm PTFE filter to remove particulate silica.

Example 3: Porous Silica Containing Particles with Polar Colorants

Silica particles were loaded with Methylene Blue colorant prior to the LPD process.

TABLE 1

Ultra II silica particle physical properties

| | |
|---|---|
| Lot # | 08K216AW |
| Diameter: | 6.3 μm |
| Average pore diameter: | 111.7 Å |
| Surface area: | 306.2 m²/g |
| Pore volume: | 0.86 cm²/g |

Five 2-gram samples of 6.3 μm HPLC particle having the physical properties set out in Table 1 above and treated in accordance with Example 1 above were dispensed into 50 mL centrifuge tubes. To each tube a molar volume of Methylene Blue stock solution was added according to the scheme in Table 2 below and the final volume of the suspension was brought up to 35 mL with deionized (DI) water. The suspensions were vibration shaken for 4 hours and centrifuged at 3000 rpm for 2 minutes. After centrifugation the silica particles collected at the bottom of the tubes. The particles were all blue in color, increasing in value with increasing colorant load. The final volume observed in the centrifuge tube was approximately 3-4 mL less in volume, indicating the colorant solution had been taken up by the dry porous particles.

After centrifugation the amount of Methylene Blue remaining in the supernatant was related to the initial [silica:Methylene Blue] mass ratio. The supernatant of the samples A and B exhibited the highest concentration of Methylene Blue remaining in the supernatant after exposure to the silica particles, with the dark blue color of the supernatant appearing nearly opaque. Supernatant in sample C exhibited a lighter, more transparent color blue and in Samples D and E the supernatant was essentially colorless.

The samples were then drained and dried in the same tubes at 70° C. for 36 hours. After drying the spherical particles retained their fluid-like properties and flowed freely when the tubes were tilted or shaken.

The LPD process employed a temperature-driven equilibrium shift in the silica solubility of the SSFA solution as described in U.S. Pat. No. 5,073,408. For the LPD process approximately 1 gram of each colored particle sample produced above was transferred to a second centrifuge tube and 35 mL of cold filtered SSFA solution (prepared as set out in Example 2 above) was added. The contents of each second tube were shaken manually for 2 minutes and placed into an oven at 20° C. for 2 hours. The oven was then heated to 30° C. for another 2 hours. Following the LPD process the tubes were immediately centrifuged at 3000 rpm for 2 minutes and the acid supernatant decanted. The samples were then rinsed six times with deionized (DI) water and dried at 70° C. overnight. After drying the pigment particles retained their fluid-like properties and flowed freely when the tubes were tilted or shaken.

Table 2 describes the experimental results. The five samples exhibited uniform blue color, with an increasing darkness value correlating with increasing initial colorant load. After rinsing and drying of the particles, the five values of blue were then matched with the standard PANTONE reference color scheme. As the concentration of the colorant in the loading procedure increases, there is also an increase in the number of water rinses required to eliminate residual Methylene Blue from the supernatant after the LPD process. In all cases after 6 rinses with deionized water the supernatants were all visibly clear, suggesting that all remaining color present in the particles was encapsulated by the LPD coating.

TABLE 2

Methylene blue doped silica particles

| Sample | Ratio of grams dry silica: moles of Methylene Blue | Aqueous supernatant color after particles were suspended in Methylene Blue solution for 4 hours | Acid supernatant color after particles were suspended in saturated fluorosilicic acid for 5.5 hours | # of water rinses until supernatant was visibly colorless (all samples were water rinsed 6 times) | Dried pigment particles color (PANTONE I.D. #) | CMYK reference to PANTONE color |
|---|---|---|---|---|---|---|
| A | 1:5 × 10⁻⁴ | Dark blue, nearly opaque | Dark blue, nearly opaque | 6 | Proc. Blue c | 100; 8.5; 0.0; 6.0 |
| B | 1:5 × 10⁻⁵ | Dark blue, nearly opaque | Dark blue, nearly opaque | 5 | 2995 c | 100; 8.5; 0.0; 0.0 |
| C | 1:5 × 10⁻⁶ | Blue, transparent | Blue, transparent | 3 | 306 c | 76; 0.0; 6.0; 0.0 |
| D | 1:1 × 10⁻⁶ | Colorless | Colorless | 0 | 310 c | 43; 0.0; 8.5; 0.0 |
| E | 1:5 × 10⁻⁷ | Colorless | Colorless | 0 | 304 c | 30.5; 0.0; 6.0; 0.0 |

As evidence of successful encapsulation from the LPD process a demonstration of increased thermal stability was performed. Methylene Blue thermally decomposes at temperatures greater than 190° C. in air. Aliquots of the five samples A-E representing particles both before and after the LPD process were loaded into ten 2 mL glass vials and heated to 200° C. for 24 hours. The color of the LPD encapsulated particles remained blue, equivalent to the assigned PANTONE color. The Methylene Blue-loaded particles without the LPD process all turned a dark purple color. Continued heating for another 24 hours had no visible effect on the LPD coated particles; however the uncoated LPD particles changed to a light brownish color, indicating a continued thermal degradation of the colorant. With further heating the uncoated LPD particles continued to fade to a very light brown.

The following method was also used to determine encapsulation: dark blue colorant loaded particles (no LPD coating) produced above in this example were immersed in 5% w/w solution of calcium hypochlorite (i.e., bleach solution) and occasionally shaken to resuspend the particles. Almost immediately the particles turned dark brown-black, followed by a progressive fading of the color until the particles were completely white. In approximately 3 hours the particles turned completely white in the presence of bleach solution. When dark blue LPD coated particles (taken from Sample A in Table 2) were immersed in bleach solution and shaken to resuspend the particles, no loss of color was observed. The colorfast properties of the LPD coated particles appeared unchanged and the experiment was terminated after seven days.

Example 4: LPD Process Used with Clean Porous Silica HPLC Particles and Rhodamine B-Doped SSFA In a single step, silica particles were loaded with Rhodamine B colorant during the LPD process. The LPD process employed is a temperature-driven equilibrium shift in the silica solubility of the SSFA solution.

TABLE 3

| Ultra II silica particle physical properties | |
|---|---|
| Lot # | 09I108AWT |
| Diameter: | 2.2 μm |
| Average pore diameter: | 110.4 Å |
| Surface area: | 297.3 m$^2$/g |
| Pore volume: | 0.77 cm$^2$/g |

A portion of the SSFA solution (prepared as set out in Example 2) was taken and 2 drops of aqueous concentrated Rhodamine B was added. After brief mixing, dry clean 2.2 μm silica particles having the physical properties set out in Table 3 above and treated in accordance with Example 1 above were added to the solution at 25° C. and stirred magnetically for a few minutes. The suspension was then placed in an oven and heated to 50° C. for 4 hours. The particles were then filtered, rinsed with deionized (DI) water, refiltered, and dried. The resulting pigment particles were pink in color resembling closest the PANTONE color 217c (CMYK: 0.0; 30.5; 0.0; 0.0).

Surface analysis of the particles prior to the LPD process was performed. BET surface area measurements of the initial untreated silica particles was 279 m$^2$/gm. Following the LPD process the final BET value was 34 m$^2$/gm, indicating the overall porosity of the particles was greatly reduced.

Example 5: Porous Silica Containing Particles with Non-Polar Colorants

This example describes colorant loading of non-polar colorants into porous silica particles, followed by encapsulation by the LPD process. Sudan Red II is slightly soluble in hexane, and is insoluble in aqueous solvents. In hexane Sudan Red II appears bright orange. Saturated Sudan Red II solutions were prepared in hexane and loaded into porous silica particles prior to LPD encapsulation.

TABLE 4

| Ultra II silica particle physical properties | |
|---|---|
| Lot # | 09J132,34 |
| Diameter: | 12.0 μm |
| Average pore diameter: | 85.99 Å |
| Surface area: | 316.11 m$^2$/g |
| Pore volume: | 0.83 cm$^2$/g |

Two 2-gram samples of dry 12 μm silica particles having the physical properties set out in Table 4 above and treated in accordance with Example 1 above were dispensed into 50 mL centrifuge tubes. To each tube 15 mL of stock saturated Sudan Red II solution in hexane was added and the tubes were shaken vigorously for 3 minutes and allowed to settle for 10 minutes. The suspensions were then centrifuged at 3000 rpm for 2 minutes. After centrifugation the silica particles collected at the bottom of the tubes. The final volume was approximately 3-4 mL less in volume than before shaking, indicating the colorant solution had been taken up by the dry porous particles. In both tubes the supernatant maintained a bright orange color, equivalent in intensity to the stock solution. The supernatant was decanted and the colored silica particles were air dried for 30 minutes, followed by 30 minutes at 100° C. in an oven. Because a portion of the colorant had penetrated into the wall of the centrifuge tube the dry colored silica particles were then transferred to a new tube.

The LPD process employed a combination of dilution-driven and temperature-driven equilibrium shifts in the silica solubility of the SSFA solution as described in U.S. Patent Publication No. 2013/0081484 A1. To the first of the two centrifuge tubes 30 mL of SSFA solution prepared as set out in Example 2 above were added. The contents of the first centrifuge tube were shaken manually for 2 minutes, and then 6 mL of deionized water were added to the first centrifuge tube. Then, the first centrifuge tube was placed into a 40° C. water bath and the contents of the first centrifuge tube were magnetically stirred for 16 hours. Following the LPD process the first centrifuge tube was immediately centrifuged at 3000 rpm for 2 minutes and the acid supernatant decanted. The aqueous acid supernatant had no visible orange color. The sample was then rinsed six times with deionized (DI) water and the supernatant was tested with litmus paper after each rinse cycle. By the sixth rinse cycle the water was essentially neutral. The encapsulated pigment particles were then dried at 70° C. overnight. After drying the pigment particles exhibited a bright orange-red color and retained their fluid-like properties and flowed freely when the tubes were tilted or shaken.

The following method was also used to determine encapsulation. Orange-red colorant loaded particles (no LPD coating) produced above in this example were immersed in 5% w/w solution of calcium hypochlorite (i.e., bleach solution) and occasionally shaken to resuspend the particles. Almost immediately a complete loss of color in the particles was observed. In less than 5 minutes the particles turned completely white in the presence of bleach solution. When Orange-red LPD coated particles produced above in this example were immersed in bleach solution and equivalently shaken to resuspend the particles, no loss of color was observed. The colorfast properties of the LPD coated particles appeared unchanged and the experiment was terminated after seven days.

Example 6: Nonporous Silica Containing Particles with Polar Colorants

In a single step, talc particles were loaded with Methylene Blue colorant during the LPD process.

TABLE 5

| 'Ultra Talc 3000' USP-grade talc particle physical properties | |
|---|---|
| Lot # | 100501 |
| Diameter: | 7.0-10 μm |
| Average pore diameter: | Essentially nonporous |
| Surface area: | 5.5 m$^2$/g |
| Pore volume: | n/a |

In this example the colorant is first dissolved in the water used to dilute the SSFA solution prepared as set out in Example 2. A 4-gram sample of dry talc particles having the physical properties set out in Table 5 above and cleaned following the steps set forth in Example 1 was dispensed into a 50 mL centrifuge tube. The LPD process employed a combination of dilution-driven and temperature-driven equilibrium shifts in the silica solubility of the SSFA solution as described in U.S. Patent Publication No. 2013/0081484 A1.

To the centrifuge tube 30 mL of SSFA solution prepared as set out in Example 2 above were added. The contents of the centrifuge tube were shaken manually for 2 minutes, and then 6 mL of 0.12M Methylene Blue solution in water were added to the centrifuge tube. Then, the contents were briefly shaken again. The centrifuge tube then was placed into a 40° C. water bath and the contents of the centrifuge tube were magnetically stirred for 19 hours. Following the LPD process the centrifuge tube was immediately centrifuged at 3000 rpm for 2 minutes and the acid supernatant decanted. The aqueous acid supernatant was nearly opaque dark blue in color. The sample was then rinsed six times with deionized (DI) water and the supernatant was tested with litmus paper after each rinse cycle. By the sixth rinse cycle the water was essentially neutral; however; it still exhibited a light blue color. The sample was rinsed an additional 2 times whereby the supernatant was essentially clear. The encapsulated pigment particles were then dried at 70° C. overnight. After drying the encapsulated pigment particles exhibited a bright blue color and flowed freely when the tubes were tilted or shaken.

The following method was also used to determine encapsulation. Bright blue colorant loaded particles (no LPD coating) were immersed in 5% w/w solution of calcium hypochlorite (i.e., bleach solution) and occasionally shaken to resuspend the particles. In approximately 8 hours the particles turned white in the presence of bleach solution. When blue LPD coated particles produced above in this example were immersed in bleach solution and equivalently shaken to resuspend the particles, no loss of color was observed. The colorfast properties of the blue LPD coated particles appeared unchanged and the experiment was terminated after seven days.

Example 7: Application of Colored Pigment Particles to Artist Media

Materials:
Linseed oil, Jack Richardson & Co., Inc.; Kimberly, Wis.
4"×4" artist stretched canvas, medium-weight archival cotton duck canvas, gesso triple primed; Art Supply Enterprises; Emeryville, Calif.
Titanium white, opaque #116 series 1; Sennelier Finest Artists' Oils, France
Preparation of Blue Paint
1.50 g titanium white paint
1.50 g linseed oil
0.520 g methylene blue pigment particles (the methylene blue LPD coated pigment paticles (the encapsulated pigment particles) produced in accordance with the invention as prepared in Example 3 (Sample B))

The methylene blue LPD coated pigment particles produced in accordance with the invention prepared in Example 3 (Sample B) mixed quickly and thoroughly in the base paint (the mixture of the titanium white paint and the linseed oil), yielding a bright uniformly blue colored paint. When applied to the artist canvas using a ¼" brush, the paint spread smoothly. Textures commonly associated with use of a paint brush were easily obtained, with no observed difference in performance in application as compared to using the base paint with no added LPD coated pigment particles.

Preparation of Red-Orange Paint
1.52 g titanium white paint
1.50 g linseed oil
1.083 g orange-red pigment particles (the orange-red LPD coated pigment particles (the encapsulated pigment particles) produced in accordance with the invention as prepared in Example 5)

The orange-red LPD coated pigment particles (that is, the encapsulated pigment particles produced in accordance with the invention) prepared in accordance with the invention as set out in Example 5 mixed quickly and thoroughly in the base paint (the mixture of the titanium white paint and the linseed oil), yielding a bright uniformly orange colored paint. When applied to the artist canvas using a palette knife, the paint spread smoothly. Textures commonly associated with use of a palette knife were easily obtained, with no observed difference in performance in application as compared to using the base paint with no added LPD coated pigment particles.

Results:

To demonstrate the pigment particles as artist media, commercially available white paint was employed as a base material. Sennelier white artists' paints are manufactured with classic artist materials including safflower oil as the base vehicle. In this way we were easily able to evaluate the mixing compatibility of the colored pigment particles and the end-use colored paint with standard classic artist media.

Blue and orange-red pigment particles, respectively were each applied to white base paint and used to cover small artist canvases. The three materials were added together on a white plastic sheet and gently worked together using a palette knife. Introduction of the particles to the base paint was very easy, with uniform colors throughout the paint obtained after less than 4 minutes of mixing. In order to maintain the soft buttery texture of the original base paint, equal amounts of linseed oil were added along with the dry particles. Application of the colored paint products using both an artist brush and palette knife was equivalent to the standard classic artist media base paint.

REFERENCES

Stober, W.; Fink, A.; Bohn, E. J. *J. Colloid Interface Sci.* 1968, v. 26, p. 62.

Foster, J; Doll, J. "Particle Size Effect on Talc Lubricant Activity". American Association of Pharmaceutical Scientists 2004 Annual Meeting Poster Session. Available online at http://www.mineralstech.com/fileadmin/user_upload/smi/Publications/S-HO-AT-PB-52.pdf

| U.S. Patent Documents | | |
|---|---|---|
| 2,490,662 | December 1949 | Thompsen, et al |
| 4,199,370 | April 1980 | Brand |
| 4,468,420 | August 1984 | Kawahara et al. |
| 4,530,725 | July 1985 | Ostertag, et al. |
| 4,851,049 | July 1989 | Wienand, et al. |
| 5,073,408 | December 1991 | Goda et al |
| 5,114,060 | May 1992 | Takemura et al. |
| 5,232,781 | August 1993 | Takemura et al. |
| 6,113,682 | November 2000 | Shin et al. |
| 6,117,435 | November 2000 | Painter et al. |
| 6,355,260 B1 | March 2002 | Tanaka et al. |
| 6,511,672 B2 | January 2003 | Tan et al. |
| 6,648,958 B2 | November 2003 | Anselmann et al. |
| 8,277,785 B2 | October 2012 | Simard et al. |
| 8,366,814 B2 | February 2013 | Jones, et al. |
| 8,658,184 | | Schulz et al. |
| 2005/0069704 A1 | Mar. 31, 2005 | Rathschlag et al. |
| 2013/0081484 A1 | December 2012 | Jones et al. |
| 2008/0044366 A1 | June 2007 | Dumousseaux |

The references listed above are each incorporated herein by reference.

The invention claimed is:

1. A method of manufacturing colored particles for use in artist color media comprising:
   (a) providing a porous silica particle having pore channels formed therein, and
   (b) depositing a silica layer over the pore channels from a silica-saturated fluorosilicic acid solution using liquid phase deposition where a colorant is present in the fluorosilicic acid solution.

2. The method of claim 1, wherein the step of depositing the silica layer over the pore channels employs reducing silica solubility of the fluorosilicic acid solution with temperature.

3. The method of claim 1, wherein the step of depositing the silica layer over the pore channels employs reducing silica solubility of the fluorosilicic acid solution with dilution.

4. The method of claim 1,
   wherein each particle has a diameter and a color value, and
   wherein the color value of each particle is controlled by the diameter of the particle.

5. The method of claim 1,
   wherein each particle has a color value and a porosity, and
   wherein the color value of each particle is controlled by the porosity of each particle or pore diameter of each particle.

6. The method of claim 1,
   wherein each particle has a color value, and
   wherein the color value of each particle is controlled by the amount of colorant present in the fluorosilicic acid solution.

7. A method of manufacturing colored particles for use in artist color media comprising:
   (a) providing a substantially nonporous silica particle, and
   (b) depositing a silica layer over the silica particle from a silica-saturated fluorosilicic acid solution using liquid phase deposition where a colorant is present in the fluorosilicic acid solution.

8. The method of claim 7, wherein the substantially nonporous silica particle is talc.

9. The method of claim 8, wherein the colored particles have a particle diameter, and
   wherein the particle diameter is between 1 micron and 100 microns.

* * * * *